(12) United States Patent
Katoh et al.

(10) Patent No.: US 10,593,072 B2
(45) Date of Patent: Mar. 17, 2020

(54) IMAGE PROCESSING APPARATUS, SURFACE ANALYZER, AND IMAGE PROCESSING METHOD

(71) Applicant: JEOL Ltd., Tokyo (JP)

(72) Inventors: Naoki Katoh, Tokyo (JP); Norihisa Mori, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 15/989,523

(22) Filed: May 25, 2018

(65) Prior Publication Data
US 2018/0342087 A1  Nov. 29, 2018

(30) Foreign Application Priority Data

May 29, 2017 (JP) ................. 2017-105804

(51) Int. Cl.
| | | |
|---|---|---|
| *G06T 11/00* | (2006.01) | |
| *G06T 11/60* | (2006.01) | |
| *G01T 1/36* | (2006.01) | |
| *G06T 11/20* | (2006.01) | |
| *G01N 23/2252* | (2018.01) | |

(52) U.S. Cl.
CPC ........ *G06T 11/005* (2013.01); *G01N 23/2252* (2013.01); *G01T 1/36* (2013.01); *G06T 11/008* (2013.01); *G06T 11/206* (2013.01); *G06T 11/60* (2013.01); *G01N 2223/402* (2013.01); *G01N 2223/605* (2013.01); *G06T 2207/10116* (2013.01)

(58) Field of Classification Search
CPC ................. G06T 11/206; G06T 11/008; G06T 2207/10061; G06T 2207/10116; G01N 2223/402; G01N 2223/408; G01N 2223/418; G01N 2223/419; G01N 2035/00891; G01N 2035/0091
See application file for complete search history.

(56) References Cited

U.S. PATENT DOCUMENTS

| | | | | |
|---|---|---|---|---|
| 6,167,362 A | * | 12/2000 | Brown ................ | G16H 50/50 703/11 |
| 2012/0230556 A1 | * | 9/2012 | Wollenweber ........ | G06T 11/008 382/128 |
| 2015/0362446 A1 | | 12/2015 | Kato et al. | |

FOREIGN PATENT DOCUMENTS

JP        2015219217 A     12/2015

* cited by examiner

*Primary Examiner* — Jeffery A Brier
(74) *Attorney, Agent, or Firm* — The Webb Law Firm

(57) ABSTRACT

An image processing apparatus including a processor and a memory, the processor executing a program stored in the memory to: acquire elemental map data representing a distribution of X-ray intensity or a distribution of concentration for each element; generate a phase map indicating a distribution of phases of compounds based on the elemental map data; and generate graphs representing X-ray intensity of each element or a concentration of each element as an area for the respective phases of the compounds included in the phase map and cause a display section to display the graphs.

7 Claims, 22 Drawing Sheets

FIG. 3

| 0 | 0 | 0 | 1 | 3 | 11 | 8 |
|---|---|---|---|---|---|---|
| 2 | 2 | 4 | 5 | 6 | 7 | 9 |
| 2 | 1 | 5 | 14 | 26 | 11 | 13 |
| 1 | 8 | 11 | 24 | 31 | 11 | 12 |
| 0 | 12 | 18 | 35 | 29 | 11 | 8 |
| 3 | 1 | 11 | 23 | 24 | 9 | 5 |

FIG. 17

IMAGE PROCESSING APPARATUS, SURFACE ANALYZER, AND IMAGE PROCESSING METHOD

CROSS-REFERENCE TO RELATED APPLICATION

This application claims priority to Japanese Patent Application No. 2017-105804 filed May 29, 2017, the disclosure of which is hereby incorporated in its entirety by reference.

BACKGROUND OF THE INVENTION

Field of the Invention

The present invention relates to an image processing apparatus, a surface analyzer, and an image processing method.

Description of Related Art

Phase analysis is known as a method of analyzing elemental map data (distribution data of X-ray intensity or concentration for each element) acquired using a surface analyzer such as an electron probe microanalyzer (EPMA). The term "phase analysis" refers to a method of extracting phases of compounds from a correlation between a plurality of elements and determining a correlation for each phase. For example, JP-A-2015-219217 discloses a method of generating a phase map indicating a distribution of a phase of a compound from elemental map data.

FIG. 24 illustrates an example of a phase map. FIG. 25 is a list of X-ray intensities of elements of each phase included in the phase map in FIG. 24.

As illustrated in FIG. 25, when the X-ray intensities of elements of each phase are displayed as a list, it is difficult to comprehend characteristics of an elemental composition of each phase. For example, with the list in FIG. 25, it is difficult to comprehend characteristics of the elemental composition of each phase such as identifying which phase has a highest X-ray intensity of Si or which phase has a lowest X-ray intensity of Al.

SUMMARY OF THE INVENTION

The invention provides an image processing apparatus capable of displaying characteristics of an elemental composition of each phase in an easily understandable manner, a surface analyzer including the image processing apparatus, and an image processing method capable of displaying characteristics of an elemental composition of each phase in an easily understandable manner.

According to a first aspect of the invention, there is provided an image processing apparatus including a processor and a memory, the processor executing a program stored in the memory to:

acquire elemental map data representing a distribution of X-ray intensity or a distribution of concentration for each element;

generate a phase map indicating a distribution of phases of compounds based on the elemental map data; and generate graphs representing X-ray intensity of each element or a concentration of each element as an area for the respective phases of the compounds included in the phase map and cause a display section to display the graphs.

According to a second aspect of the invention, there is provided a surface analyzer including the image processing apparatus described above.

According to a third aspect of the invention, there is provided an image processing method including:

acquiring elemental map data representing a distribution of X-ray intensity or a distribution of concentration for each element;

generating a phase map indicating a distribution of phases of compounds based on the elemental map data; and generating graphs representing X-ray intensity of each element or a concentration of each element as an area for the respective phases of the compounds included in the phase map and causing a display section to display the graphs.

BRIEF DESCRIPTION OF THE DRAWINGS

FIG. 3 is a table illustrating results of a principal component analysis.

FIG. 17 illustrates how the peak detected in FIG. 16 is determined.

DESCRIPTION OF THE INVENTION

According to one embodiment of the invention, there is provided an image processing apparatus including a processor and a memory, the processor executing a program stored in the memory to:

acquire elemental map data representing a distribution of X-ray intensity or a distribution of concentration for each element;

generate a phase map indicating a distribution of phases of compounds based on the elemental map data; and generate graphs representing X-ray intensity of each element or a concentration of each element as an area for the respective phases of the compounds included in the phase map and cause a display section to display the graphs.

Such an image processing apparatus causes the display section to display the graphs representing X-ray intensity of each element or a concentration of each element as an area for the respective phases of the compounds included in the phase map. Therefore, a user can readily comprehend characteristics of an elemental composition of each phase.

According to one embodiment of the invention, there is provided a surface analyzer including the image processing apparatus described above.

According to one embodiment of the invention, there is provided an image processing method including:

acquiring elemental map data representing a distribution of X-ray intensity or a distribution of concentration for each element;

generating a phase map indicating a distribution of phases of compounds based on the elemental map data; and generating graphs representing X-ray intensity of each element or a concentration of each element as an area for the respective phases of the compounds included in the phase map and causing a display section to display the graphs.

Such an image processing method causes the display section to display the graphs representing X-ray intensity of each element or a concentration of each element as an area for the respective phases of the compounds included in the phase map. Therefore, a user can readily comprehend characteristics of an elemental composition of each phase.

Embodiments of the invention are described in detail below with reference to the drawings. Note that the following embodiments do not unduly limit the scope of the invention as stated in the claims. In addition, all of the elements described in connection with the following embodiments should not necessarily be taken as essential requirements of the invention.

1. Surface Analyzer

Figure 1:
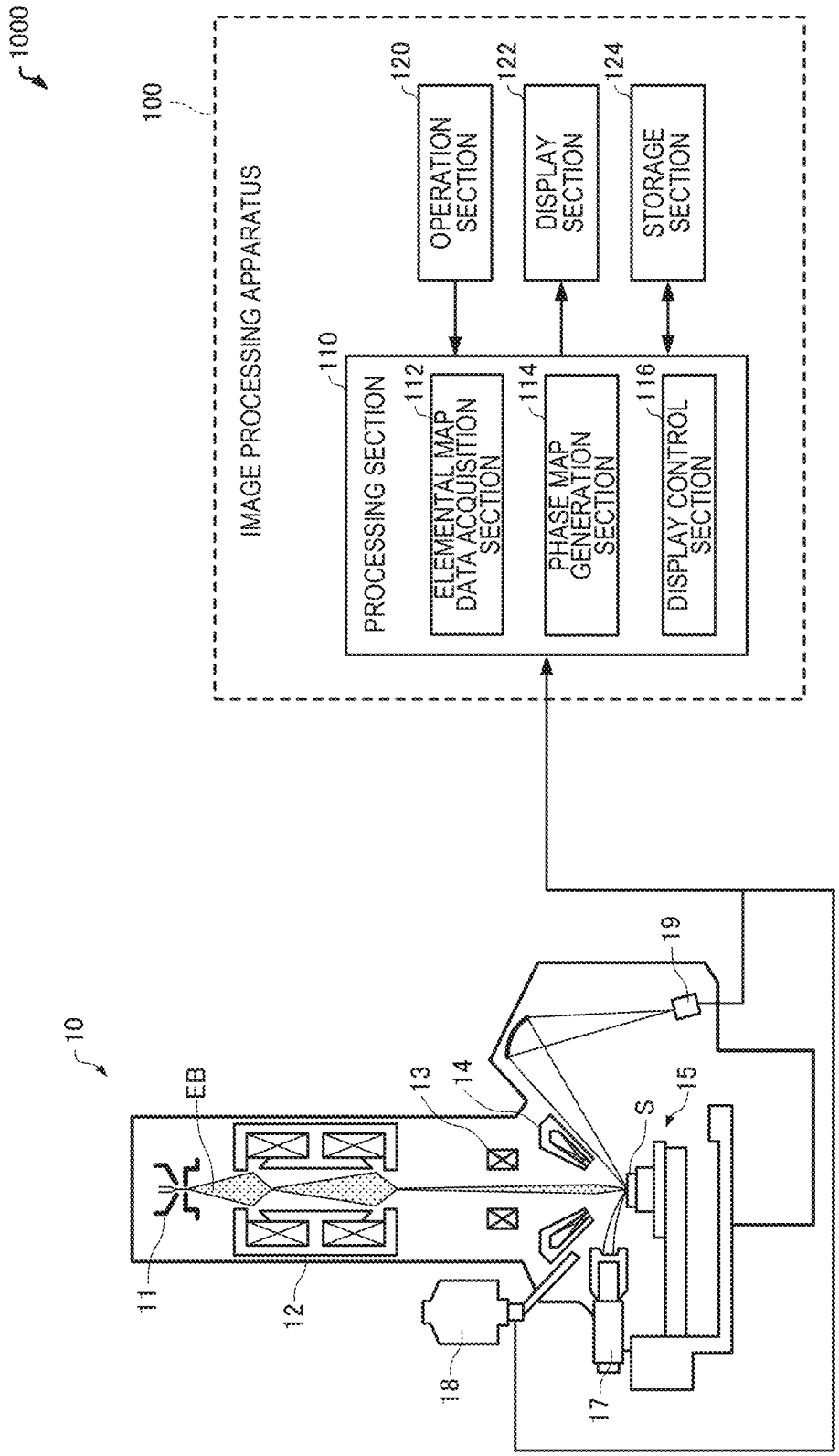
FIG. 1 schematically illustrates a configuration of a surface analyzer that includes an image processing apparatus according to one embodiment of the invention.

First, an image processing apparatus according to one embodiment of the invention will be described with reference to the drawings. A case where the image processing apparatus is built into a surface analyzer will now be described. FIG. 1 illustrates a configuration of a surface analyzer 1000 according to one embodiment of the invention.

The surface analyzer 1000 is an apparatus which applies electron beams EB to a sample S, detects characteristic X-rays that are generated from the sample S due to the application of the electron beams EB, and qualitatively or quantitatively analyzes an element included in the sample S. The surface analyzer 1000 can also perform an area analysis (a map analysis) on the sample S. The surface analyzer 1000 is an electron probe microanalyzer (EPMA), for example.

As illustrated in FIG. 1, the surface analyzer 1000 includes a surface analyzer main body 10 and an image processing apparatus 100.

1.1 Surface Analyzer Main Body

The surface analyzer main body 10 includes an electron gun 11, a condenser lens 12, a deflector 13, an objective lens 14, a sample stage 15, a secondary electron detector 17, an energy-dispersive X-ray detector 18, and a wavelength-dispersive X-ray spectrometer 19.

The electron gun 11 generates electron beams EB. The electron gun 11 emits the electron beams EB that have been accelerated by applying a predetermined accelerating voltage toward the sample S.

The condenser lens 12 is a lens for causing the electron beam EB emitted from the electron gun 11 to converge.

The deflector 13 is capable of deflecting the electron beams EB. A scan signal is input to the deflector 13 through a control circuit (not illustrated), and the sample S can be scanned with the electron beams EB (an electron probe) that have been focused by the condenser lens 12 and the objective lens 14.

The objective lens 14 is a lens for focusing the electron beams EB on the sample S to apply the electron beams EB to the sample S as an electronic probe.

The sample stage 15 is capable of supporting the sample S. The sample S is placed on the sample stage 15. The sample stage 15 is moved by a stage-moving mechanism (not illustrated in FIG. 1) that includes a drive source (e.g., motor). An analysis position (a position to which the electron beams EB (the electronic probe) are applied) on the sample S can be moved by moving the sample stage 15.

The secondary electron detector 17 is a detector for detecting secondary electrons released from the sample S. A secondary electron image (a SEM image) can be obtained from a signal output from the secondary electron detector 17. The signal output from the secondary electron detector 17 is sent to a processing section 110 and stored in a storage section 124 as image data that is synchronized with the scan signal for the electron beams EB.

The energy-dispersive X-ray detector 18 is a detector for discriminating X-rays according to energy to obtain a spectrum. The energy-dispersive X-ray detector 18 detects characteristic X-rays that are generated when the electron beams EB have been applied to the sample S.

The wavelength-dispersive X-ray spectrometer 19 is constituted by a spectroscopic element (an analyzing crystal) and an X-ray detector. The wavelength-dispersive X-ray spectrometer 19 isolates a characteristic X-ray generated from the sample S into an X-ray with a specific wavelength using a Bragg reflection at the spectroscopic element and detects the isolated X-ray with the X-ray detector.

The surface analyzer main body 10 can perform a map analysis (an area analysis) on the sample S. Specifically, the surface analyzer main body 10 divides a designated range of the sample S into predetermined pixels (unit areas), and measures the X-ray intensity at each pixel using the energy-dispersive X-ray detector 18 (or the wavelength-dispersive X-ray spectrometer 19) to obtain elemental map data (elemental distribution information).

Elemental map data is data including includes two-dimensional distribution information about an element. The elemental map data includes information about a two-dimensional position (coordinates) and X-ray intensity at each position. In addition, by converting the X-ray intensity at each position into a concentration of an element at each position, elemental map data indicating positions on the sample S and a concentration of an element at each position can be obtained. The elemental map data is obtained for each element.

1.2 Image Processing Apparatus

The image processing apparatus 100 acquires elemental map data and performs a phase analysis. In addition, the image processing apparatus 100 displays a phase map on a display section 122. Furthermore, the image processing apparatus 100 displays a pie chart representing X-ray intensities of elements on the display section 122 for each phase of a compound included in the phase map. The term "phase analysis" as used herein refers to a method of extracting a phase of a compound from a correlation between a plurality of elements and determining a correlation for each phase. The image processing apparatus 100 is implemented by a general-purpose computer such as a personal computer (PC), for example. The image processing apparatus 100 includes the processing section 110, an operation section 120, the display section 122, and the storage section (a memory) 124.

The operation section 120 acquires an operation signal that corresponds to an operation performed by the user, and transmits the operation signal to the processing section 110. The operation section 120 is implemented by a button, a key, a touch panel display, or a microphone, for example.

The display section 122 displays an image generated by the processing section 110.

The function of the display section 122 can be implemented by an LCD, a CRT, or the like. For example, a phase map generated by the processing section 110 (a phase map generation section 114) and parameters and the like in phase analysis including a pie chart representing an X-ray intensity of each element of a phase are displayed on the display section 122. The display section 122 also displays a secondary electron image, an elemental map, and the like.

The storage section 124 stores a program, data, and the like that cause or allow the processing section 110 to perform various calculation processes. The storage section 124 is used as a work area for the processing section 110, and temporarily stores results of calculations performed by the processing section 110 according to a program, and the like. The function of the storage section 124 can be realized by a hard disk, a RAM, or the like.

The processing section 110 performs various calculation processes according to the program stored in the storage section 124. The processing section 110 functions as an elemental map data acquisition section 112, the phase map generation section 114, and a display control section 116 to be described below by executing the program stored in the storage section 124. The function of the processing section 110 may be implemented by hardware such as a processor (e.g., CPU or DSP) or ASIC (e.g., gate array), or by a program. Note that at least part of the processing section 110 may be implemented by hardware (a dedicated circuit). The processing section 110 includes the elemental map data acquisition section 112, the phase map generation section 114, and the display control section 116.

The elemental map data acquisition section 112 acquires a plurality of pieces of elemental map data. For example, when the user has selected some pieces of elemental map data from a plurality of pieces of elemental map data obtained by an area analysis performed by the surface analyzer main body 10, the elemental map data acquisition section 112 reads the selected elemental map data from the storage section 124. The user selects a desired piece of elemental map data from a plurality of pieces of elemental map displayed on the display section 122, for example.

Figure 2:
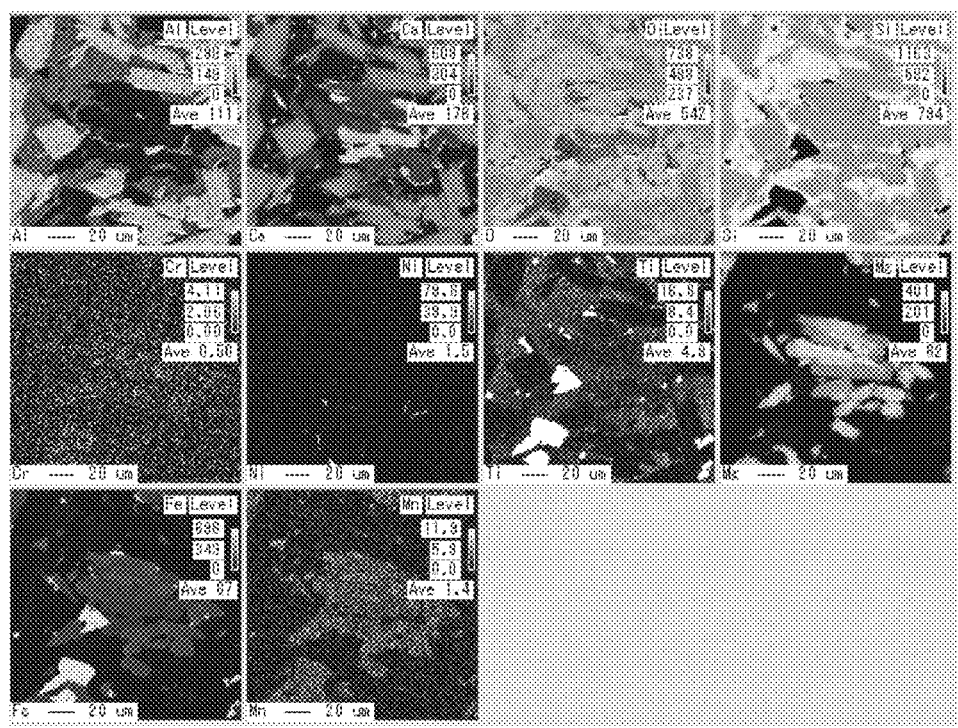
FIG. 2 illustrates an example of elemental map data acquired by an elemental map data acquisition section.

FIG. 2 illustrates an example of the elemental map data acquired by the elemental map data acquisition section 112. In the example illustrated in FIG. 2, Al elemental map data, Ca elemental map data, O elemental map data, Si elemental map data, Mn elemental map data, Fe elemental map data, Ni elemental map data, Ti elemental map data, Mg elemental map data, and Cr elemental map data have been acquired by the elemental map data acquisition section 112.

The phase map generation section 114 generates a phase map from a plurality of pieces of elemental map data acquired by the elemental map data acquisition section 112. Hereinafter, a process performed by the phase map generation section 114 to generate a phase map will be described.

The phase map generation section 114 performs a principal component analysis on elemental map data acquired by the elemental map data acquisition section 112 to calculate a principal component score for each pixel (unit area) of the elemental map data.

The term "principal component analysis" as used herein refers to a multivariate analysis method of calculating a small number of characteristic variables (composite variables) from multivariate data, the characteristic variables representing characteristics of a data set. A composite variable (a principal component) u is represented by the following expression:

$$u_i = a_1 x_{1,i} + a_2 x_{2,i} + \ldots + a_{N-1} x_{N-1,i} + a_N x_{N,i}$$

where N is the number of variables, i is a natural number, x is data of each variable, and $a_1$, $a_2$ ... $a_{N-1}$, and $a_N$ are composite variable coefficients.

The composite variable coefficients $a_1$, $a_2$, ..., $a_{N-1}$, and $a_N$ are calculated so that a variance of the composite variable u becomes a maximum. Note that the composite variable coefficients satisfy the following relationship.

$$a_1^2 + a_2^2 + \ldots + a_{N-1}^2 + a_N^2 = 1$$

When calculating the composite variable coefficients $a_1$, $a_2$ ... $a_{N-1}$, and $a_N$, a variance-covariance matrix of an original data set is calculated, and an eigenvalue problem of the variance-covariance matrix is solved. An eigenvector that is a solution to the eigenvalue problem corresponds to the coefficients $a_1$, $a_2$ ... $a_{N-1}$, and $a_N$. The resulting N-number (i.e., the same number as the number of pieces of data included in the original data set) of principal components include a first principal component, a second principal component ... and an Nth principal component (in a descending order of eigenvalues).

Figure 3:
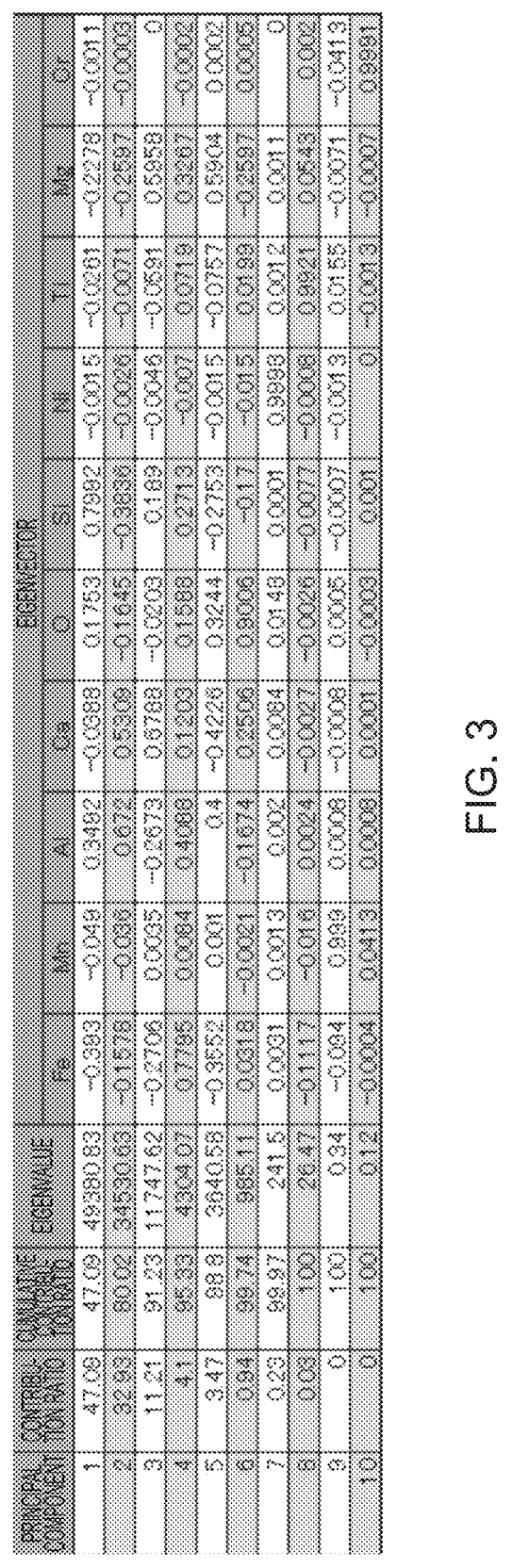

The phase map generation section 114 performs the principal component analysis on data (an intensity value or a concentration value) of each pixel of the elemental map data acquired by the elemental map data acquisition section 112. FIG. 3 illustrates a table that indicates results of the principal component analysis. Information about a contribution ratio, a cumulative contribution ratio, an eigenvalue, and an eigenvector (see FIG. 3) is obtained for each principal component as a result of the principal component analysis performed by the phase map generation section 114. When the principal component analysis is performed on ten pieces of elemental map data (see FIG. 2), information about a first principal component to a tenth principal component is obtained (see FIG. 3).

The phase map generation section 114 calculates a principal component score for each pixel of each piece of elemental map data using the eigenvector (see FIG. 3). Accordingly, a principal component score map data for each principal component is generated. A principal component score can be calculated using the following expression:

$$u_i = a_1(x_{1,i} - \overline{x_1}) + a_2(x_{2,i} - \overline{x_2}) + \ldots + a_N(x_{N,i} - \overline{x_N})$$

where a is an eigenvector, x is data (an intensity value or a concentration value) of each pixel, i is 1 to a total number of pixels, N is a total number of elements, and $\overline{x}_k$ is an average value (an average intensity value or an average concentration value) of each piece of elemental map data.

Note that the average value of each piece of elemental map data is subtracted from the data of each pixel so that the principal component score corresponds to the origin 0 when the data of each pixel corresponds to the average value.

For example, the principal component score of the first principal component (first principal component score) can be calculated by the following expression using the results of the principal component analysis in FIG. 3:

$$u_1 = -0.393 \times (Fe - \overline{Fe}) - 0.0049 \times (Mn - \overline{Mn}) + 0.3492 \times (Al - \overline{Al}) - 0.0388 \times (Ca - \overline{Ca}) + 0.1753 \times (O - \overline{O}) + 0.7992 \times (Si - \overline{Si}) - 0.0015 \times (Ni - \overline{Ni}) - 0.0261 \times (Ti - \overline{Ti}) - 0.2278 \times (Mg - \overline{Mg}) - 0.0011 \times (Cr - \overline{Cr})$$

where "Fe" is data (an intensity value or a concentration value) of each pixel of Fe elemental map data, and "$\overline{Fe}$" is an average value of the data (the intensity value or the concentration value) of each pixel of the Fe elemental map data. These definitions also apply to the other elements.

Figure 4:
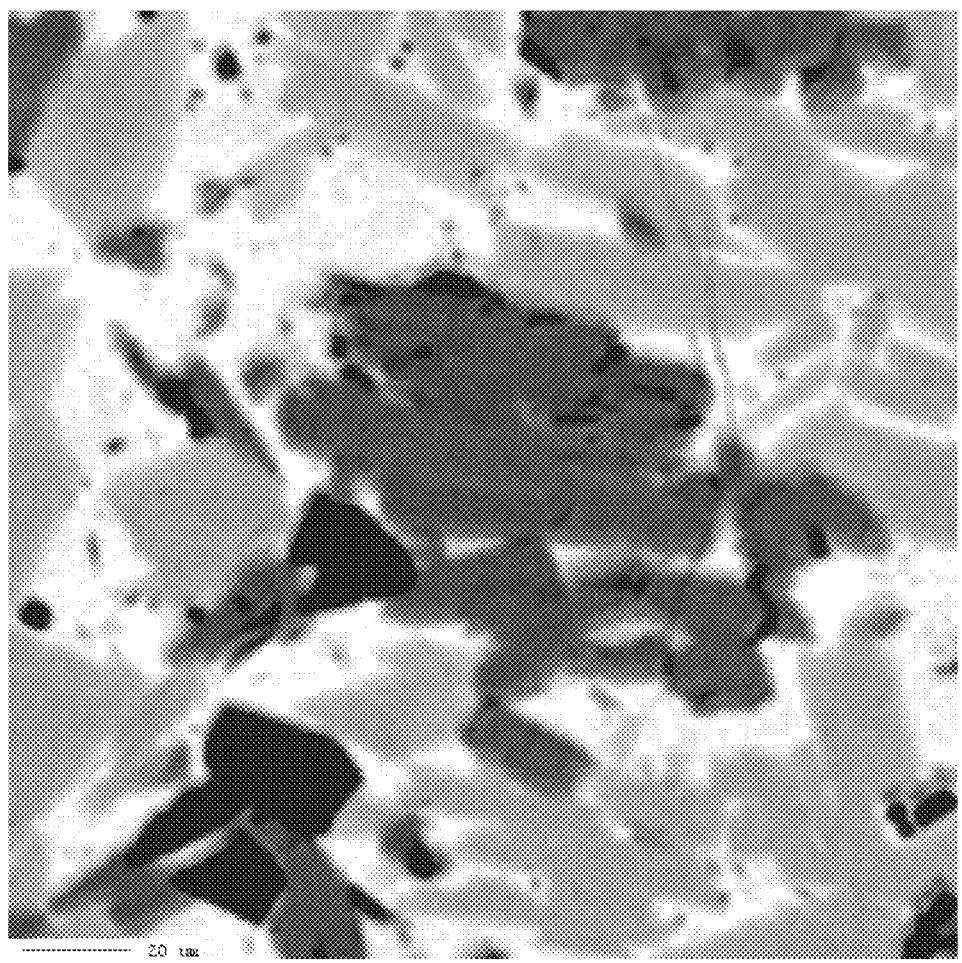
FIG. 4 illustrates principal component score map data of a first principal component score.

The phase map generation section 114 generates the principal component score map data of the first principal component from the data of the principal component score calculated for each pixel using the above expression. The principal component score map data represents the principal component score calculated for each pixel in the form of map data (i.e., data that represents a position and a principal component score at the corresponding position). FIG. 4 illustrates principal component score map data of the first principal component score.

Figure 5:
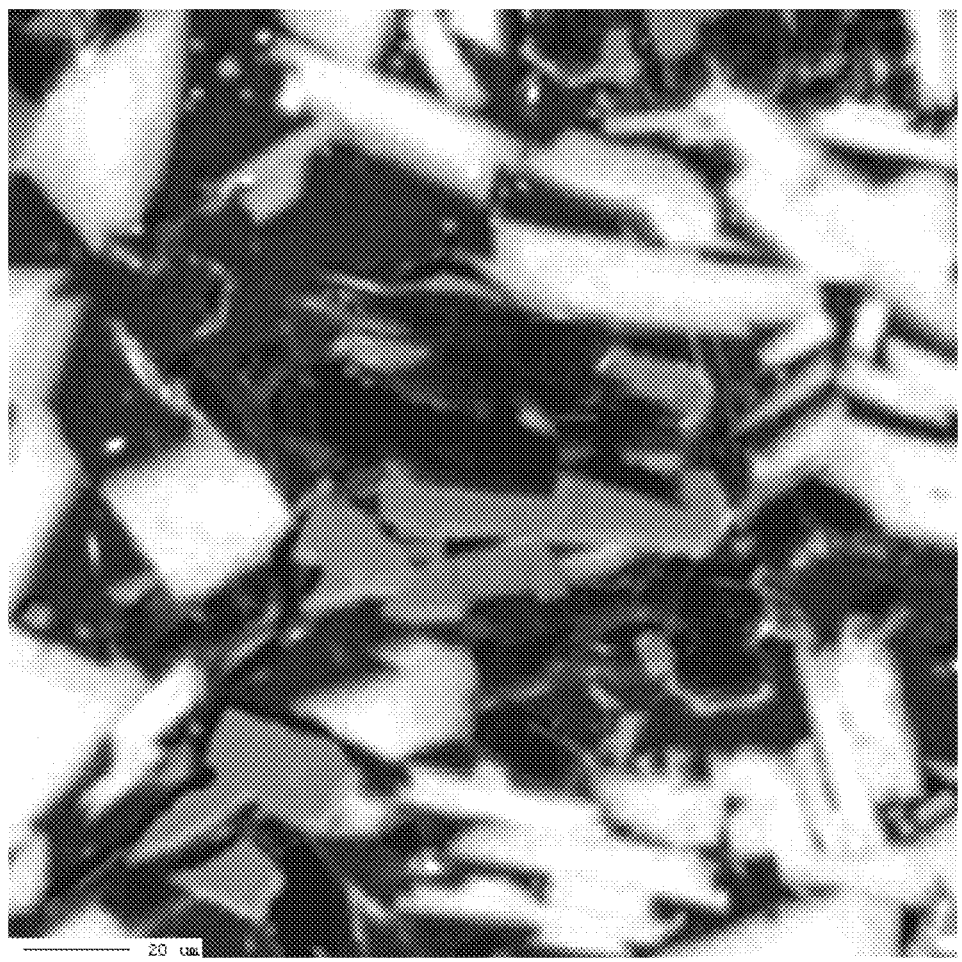
FIG. 5 illustrates principal component score map data of a second principal component score.
Figure 6:
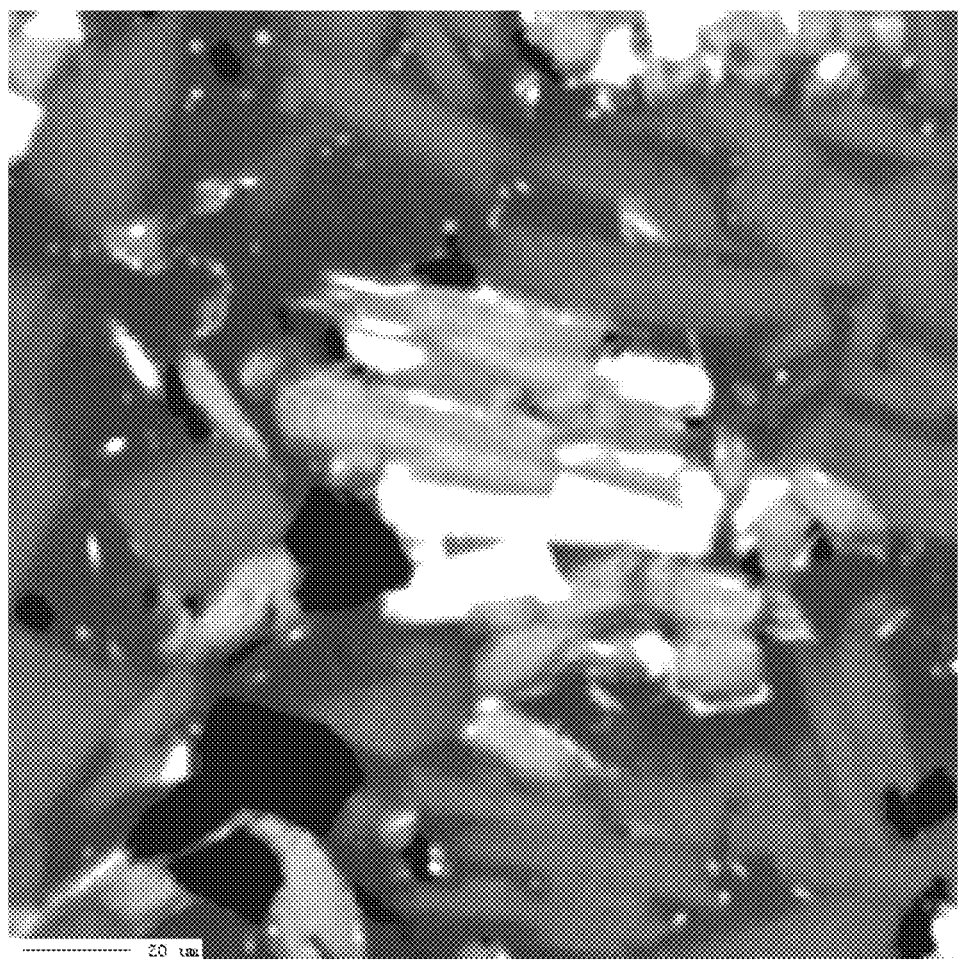
FIG. 6 illustrates principal component score map data of a third principal component score.
Figure 7:
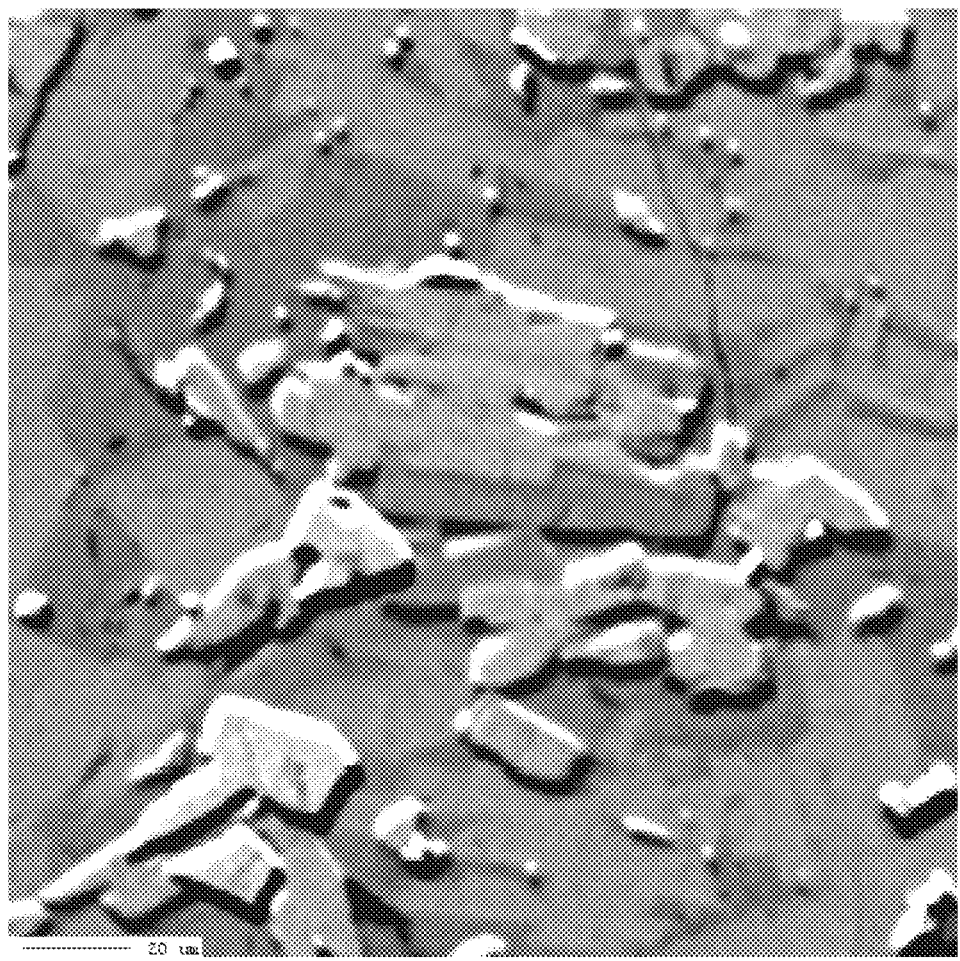
FIG. 7 illustrates principal component score map data of a fourth principal component score.
Figure 8:
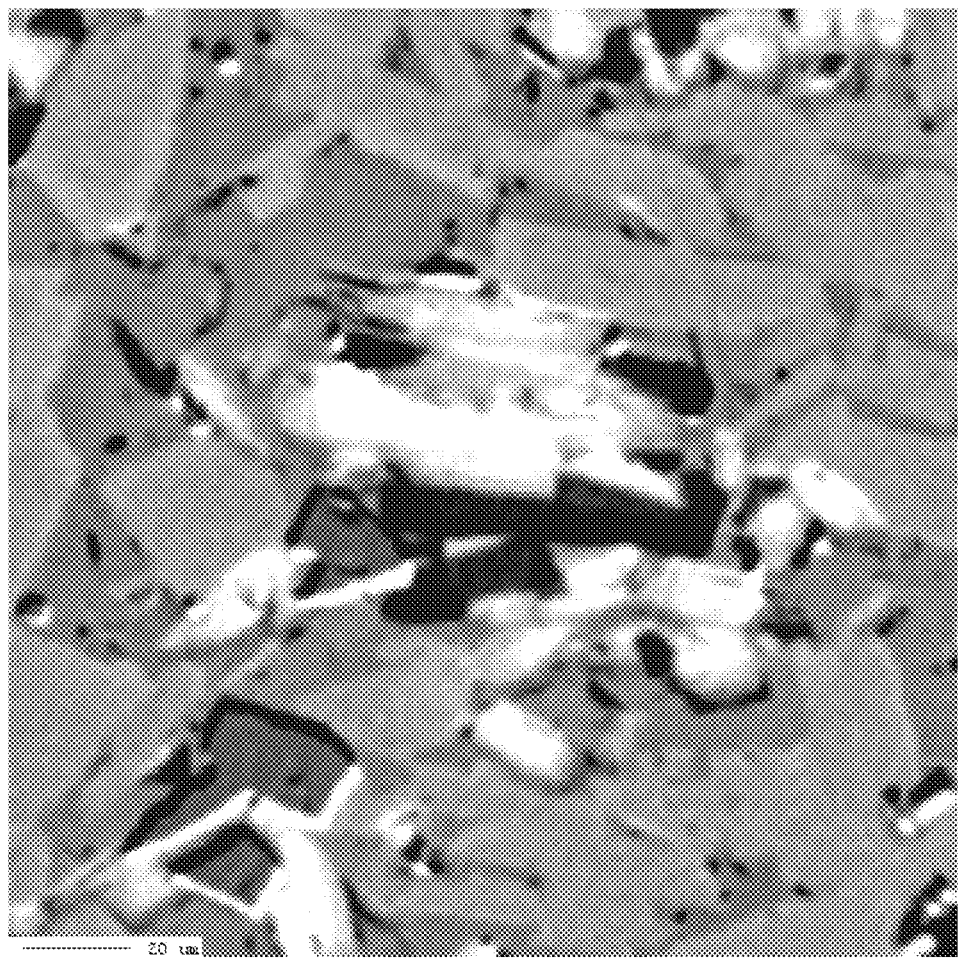
FIG. 8 illustrates principal component score map data of a fifth principal component score.
Figure 9:
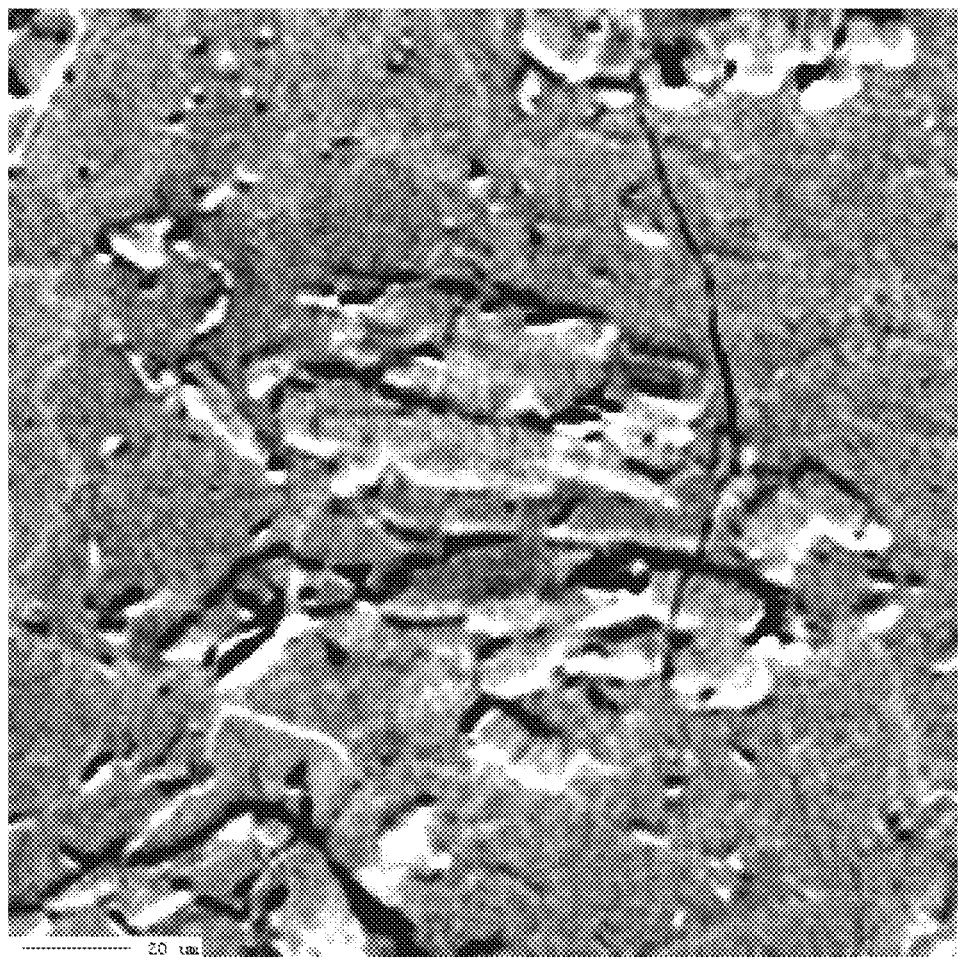
FIG. 9 illustrates principal component score map data of a sixth principal component score.
Figure 10:
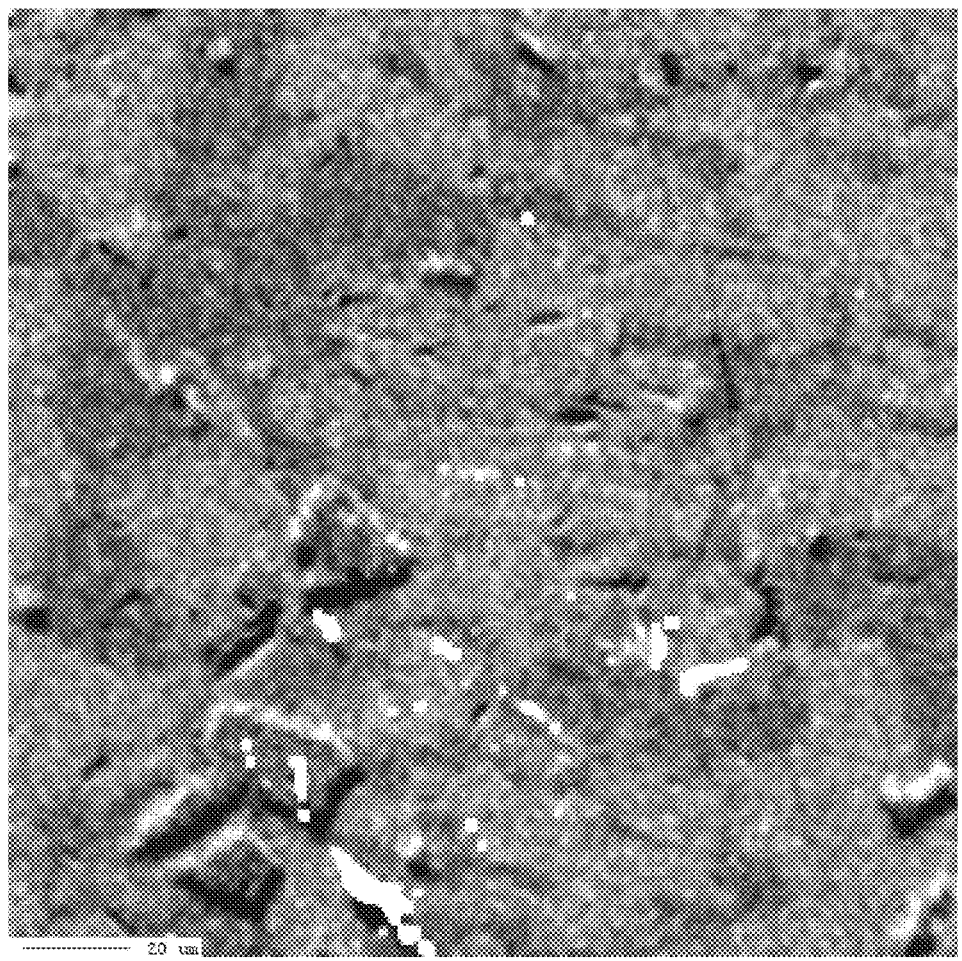
FIG. 10 illustrates principal component score map data of a seventh principal component score.
Figure 11:
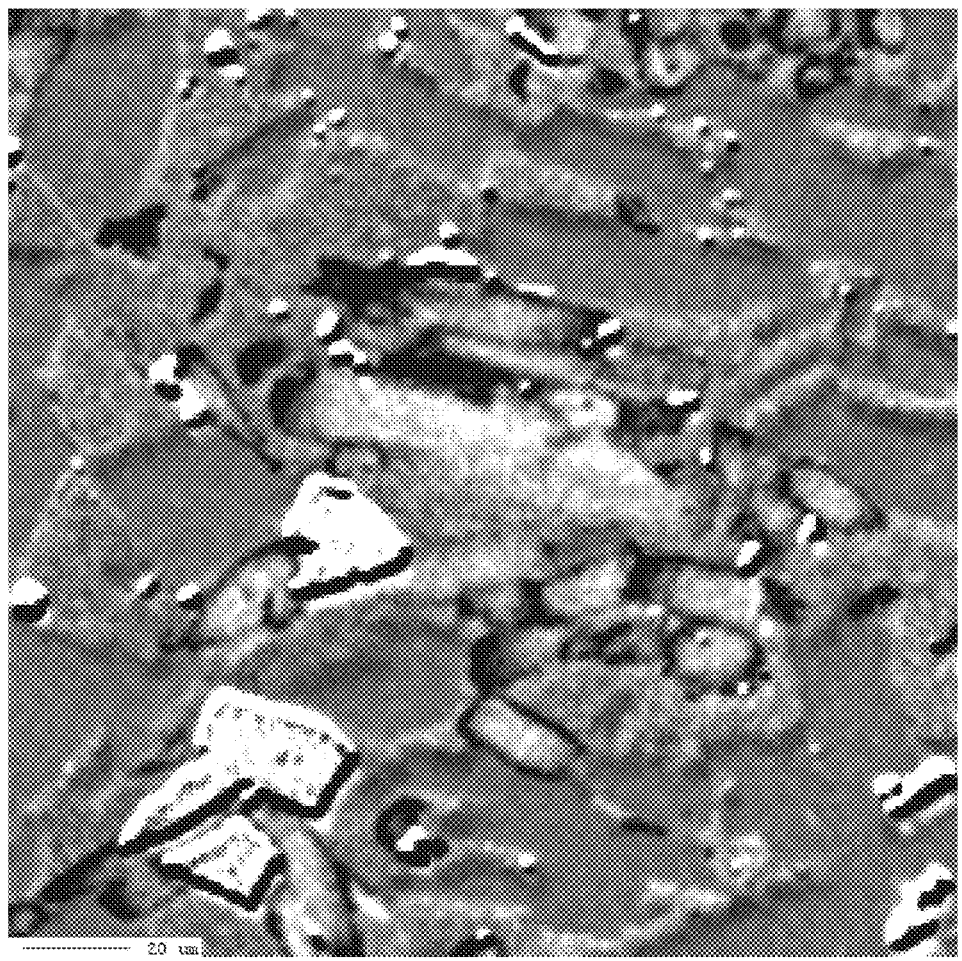
FIG. 11 illustrates principal component score map data of an eighth principal component score.
Figure 12:
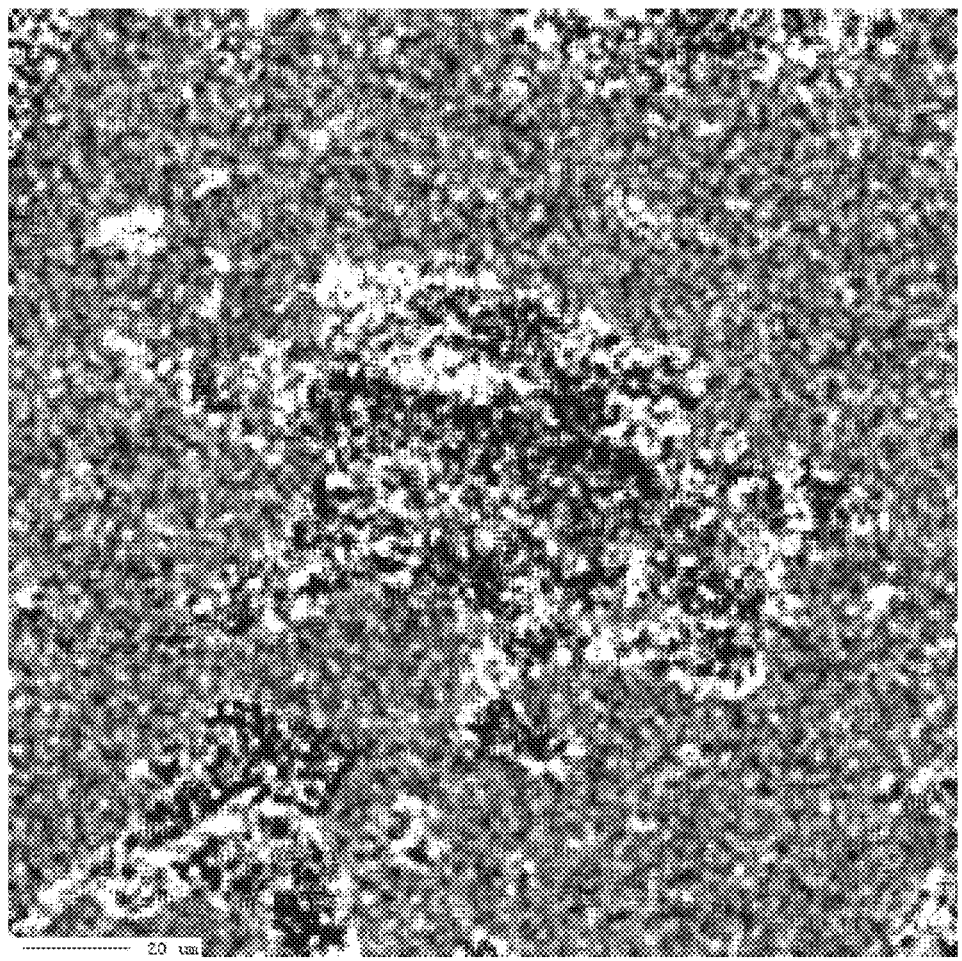
FIG. 12 illustrates principal component score map data of a ninth principal component score.
Figure 13:
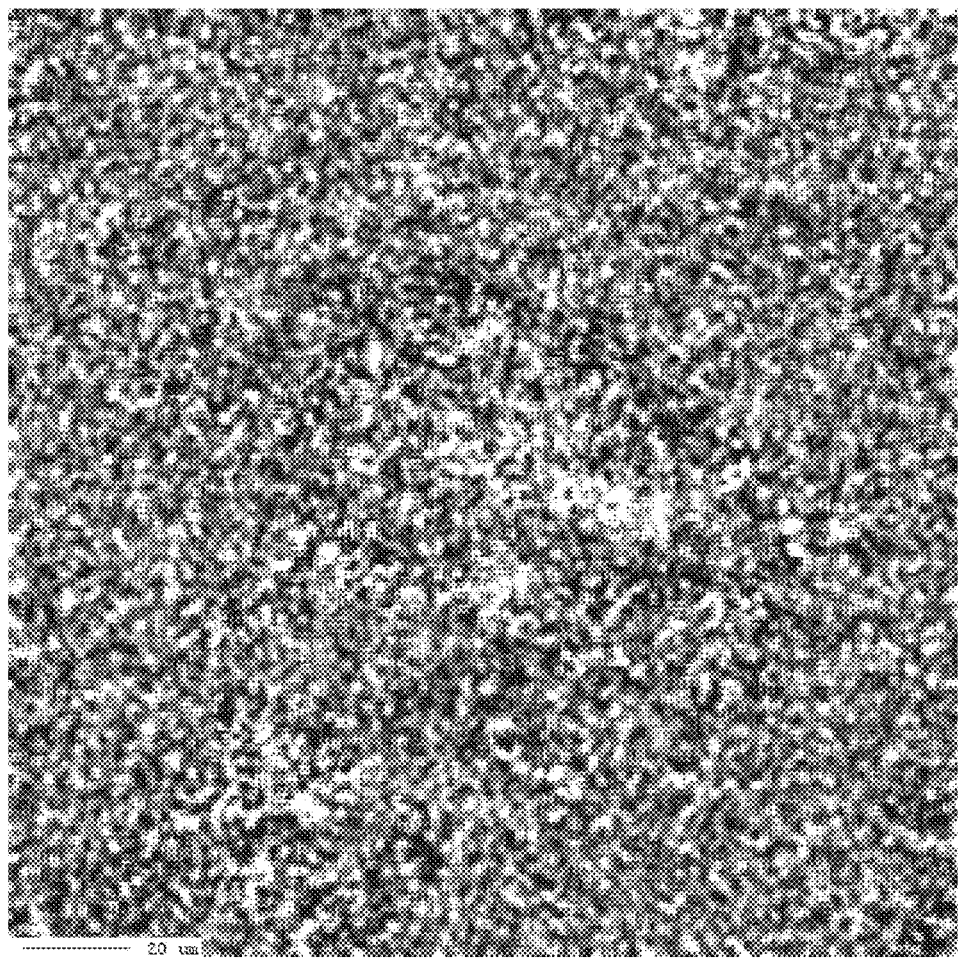
FIG. 13 illustrates principal component score map data of a tenth principal component score.

The phase map generation section 114 generates the principal component score map data as described above for the second to tenth principal components. FIG. 5 illustrates principal component score map data of the second principal component score. FIG. 6 illustrates principal component score map data of the third principal component score. FIG. 7 illustrates principal component score map data of the fourth principal component score. FIG. 8 illustrates principal component score map data of the fifth principal component score. FIG. 9 illustrates principal component score map data of the sixth principal component score. FIG. 10 illustrates principal component score map data of the seventh principal component score. FIG. 11 illustrates principal component score map data of the eighth principal component score. FIG. 12 illustrates principal component score map data of the ninth principal component score. FIG. 13 illustrates principal component score map data of the tenth principal component score.

The phase map generation section 114 plots the calculated principal component scores to generate a principal component score scatter diagram. Specifically, first, a principal component having a large eigenvalue is selected. For example, a principal component is selected so that a cumulative contribution ratio is equal to or larger than a predetermined value (e.g., 80%). In the example illustrated in FIG. 3, since the cumulative contribution ratio corresponding to the first and second principal components exceeds 80%, the phase map generation section 114 selects the first principal component and the second principal component. Note that the method of selecting a principal component is not limited thereto, and a principal component having an eigenvalue equal to or larger than 1 may be selected or a principal component having a contribution ratio equal to or larger than a predetermined value may be selected.

Figure 14:
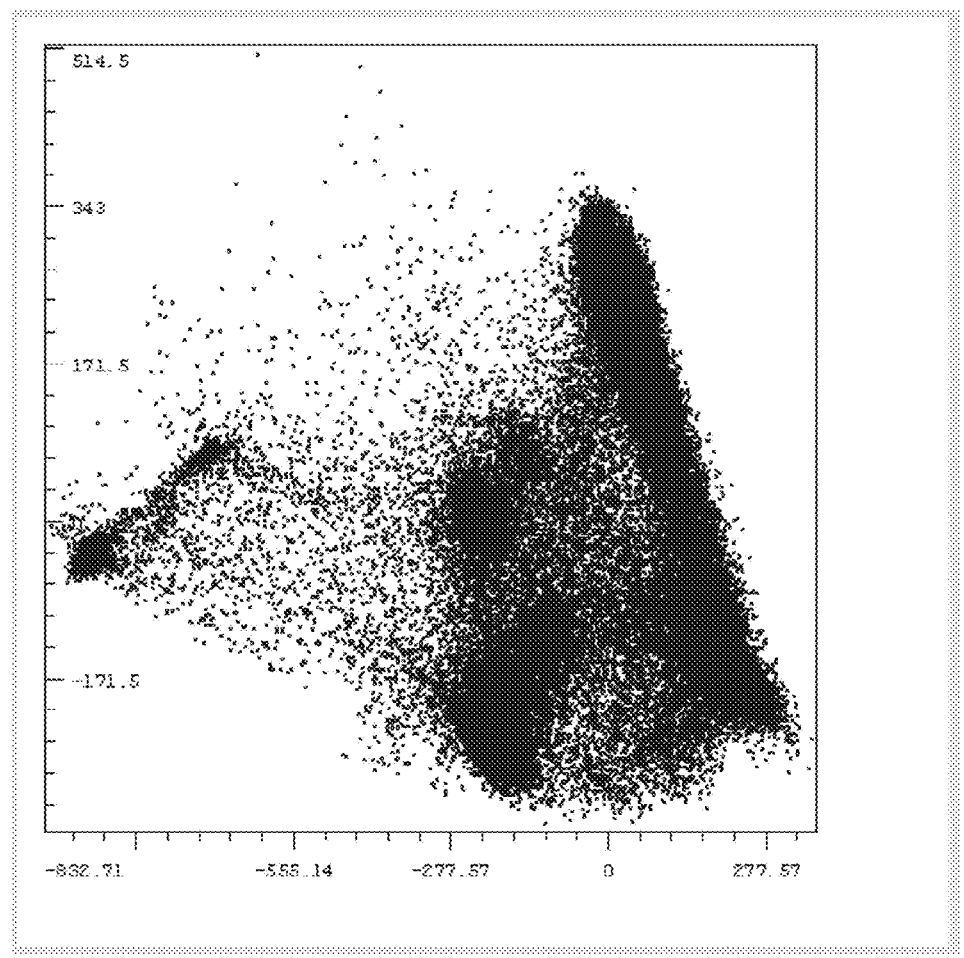
FIG. 14 illustrates an example of a principal component score scatter diagram.

Next, the phase map generation section 114 generates a principal component score scatter diagram using the selected principal components. For example, when the phase map generation section 114 has selected the first principal component and the second principal component, the phase map generation section 114 plots a value of the first principal component score and a value of the second principal component score (that correspond to each pixel of the elemental map data) on a scatter diagram in which the horizontal axis indicates the first principal component score, and the vertical axis indicates the second principal component score. The phase map generation section 114 thus generates the principal component score scatter diagram. FIG. 14 illustrates an example of the principal component score scatter diagram. In the scatter diagram illustrated in FIG. 14, the horizontal axis indicates the first principal component score, and the vertical axis indicates the second principal component score.

Although an example in which the first principal component and the second principal component are selected to generate a two-dimensional scatter diagram has been described above, the first to nth (n<N) principal components may be selected to generate an n-dimensional scatter diagram.

The phase map generation section 114 detects a peak position from the principal component score scatter diagram. The peak position is a center-of-gravity position of each cluster (each group) (i.e., a representative position of each cluster) on the principal component score scatter diagram. For example, the phase map generation section 114 divides the principal component score scatter diagram into a plurality of areas, counts the number of data points within each area to calculate a point density, and detects the peak position based on the point density. In addition, for example, areas among contiguous areas that have high point density may be determined as peak position candidates, and a peak position candidate that has a point density equal to or higher than a threshold value among the peak position candidates may be determined as a peak position. Hereinafter, a process of detecting a peak position from a principal component score scatter diagram will be described in detail.

Figure 15:
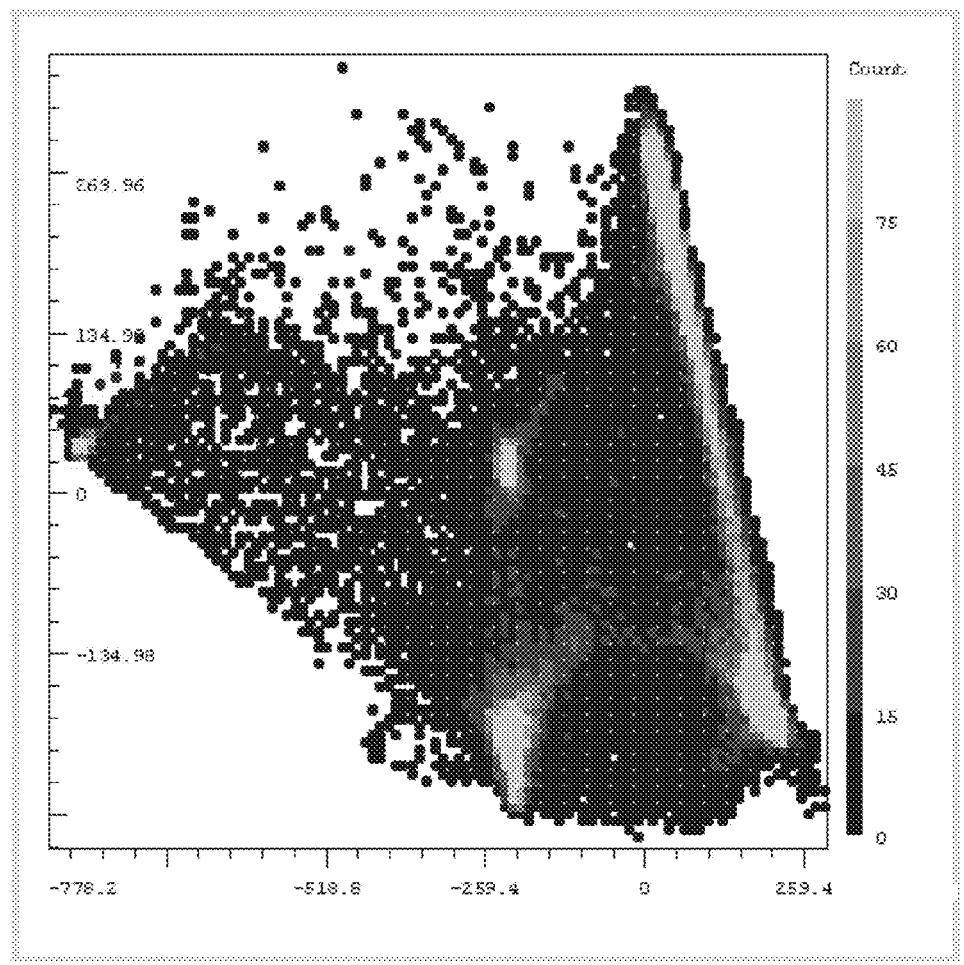
FIG. 15 illustrates a principal component score scatter diagram that is displayed using point density.

First, a process of displaying a principal component score scatter diagram using point density is performed. FIG. 15 illustrates the principal component score scatter diagram that is displayed using the point density. In the example illustrated in FIG. 15, the principal component score scatter diagram illustrated in FIG. 14 is divided into 100×100 areas, and the number of data points (point density) that has been counted within each area is displayed. In FIG. 15, the point density (i.e., the number of data points) is indicated by shading.

Figure 16:
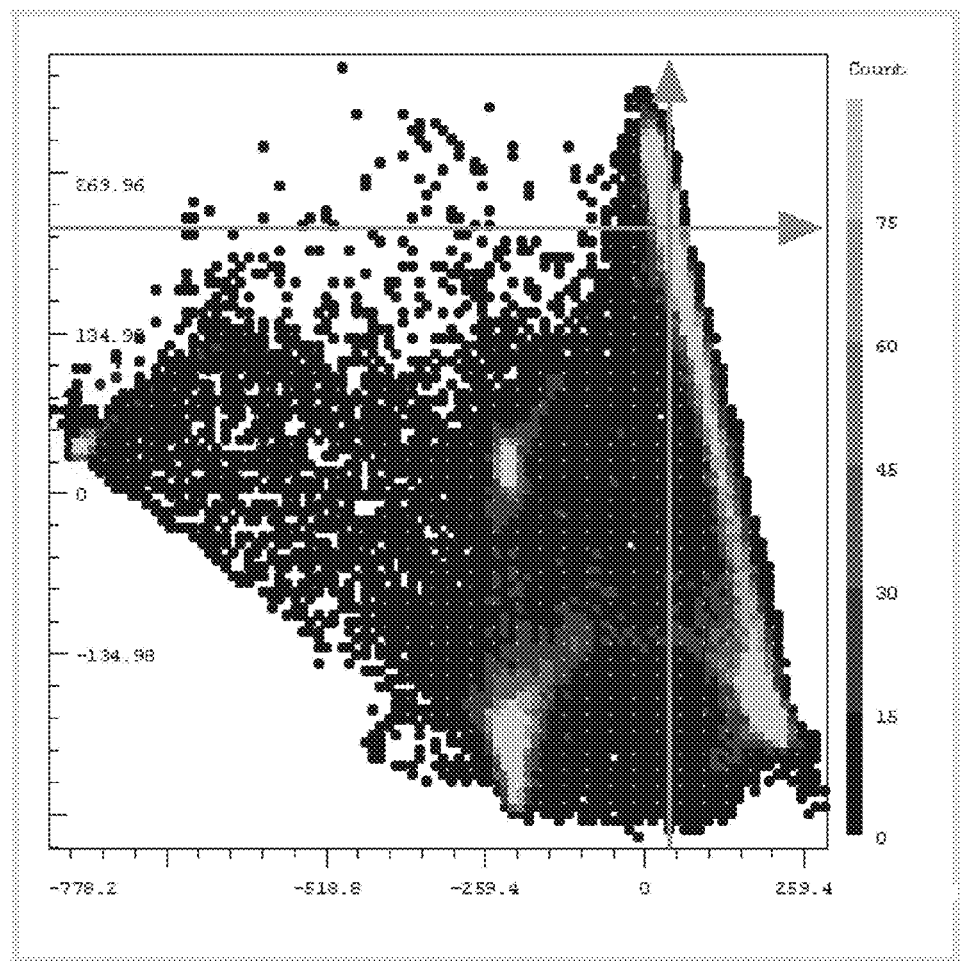
FIG. 16 illustrates how a peak (a point with high density) of data is searched on a principal component score scatter diagram.

As illustrated in FIG. 16, the phase map generation section 114 searches the scatter diagram displayed using the point density for the peak position in the horizontal axis direction. When the phase map generation section 114 searches the scatter diagram in the horizontal axis direction, the phase map generation section 114 determines an area in which the number of data points is larger than that of the areas contiguous thereto in the horizontal axis direction to be the peak position. FIG. 17 illustrates part of the data of the scatter diagram displayed using the point density. In FIG. 17, each value represents the number of data points.

When the phase map generation section 114 has found an area that is considered to be the peak position by searching the scatter diagram in the horizontal axis direction, the phase map generation section 114 searches the scatter diagram for the peak position in the vertical axis direction so as to pass through the area (considered to be the peak position) that has been found by searching the scatter diagram in the horizontal axis direction. When the phase map generation section 114 searches the scatter diagram in the vertical axis direction, the phase map generation section 114 determines an area in which the number of data points is larger than that of the areas contiguous thereto in the vertical axis direction to be the peak position. The phase map generation section 114 determines an area (indicated by the diagonal lines that extend from upper right to lower left in FIG. 17) that has been determined to be the peak position by both the search process in the horizontal axis direction and the search process in the vertical axis direction to be a peak position candidate.

The phase map generation section 114 performs the above process on the entire scatter diagram (displayed using the point density) in order to find peak position candidates. In the example illustrated in FIG. 17, five areas have been determined to be peak position candidates.

Note that the phase map generation section 114 may perform a process of smoothing the scatter diagram (displayed using the point density) before performing the process of searching the scatter diagram for peak position candidates. This makes it possible to reduce the probability that two contiguous peaks have the same value (i.e., the same number of data points).

The phase map generation section 114 then performs a narrow-down process on the peak position candidates that have been found by the above process. The phase map generation section 114 passes over a peak position candidate among the peak position candidates that have been found by the above process in which the number of data points is less than a threshold value. Specifically, the phase map generation section 114 selects and determines a peak position candidate among the peak position candidates that have been found by the above process in which the number of data points is equal to or larger than the threshold value to be the peak position. The threshold value may be arbitrarily set. For example, the threshold value is set to ⅕ of the maximum number of data points. Note that the threshold value may be set in accordance with the maximum number of data points.

When an area in which the number of data points is larger than that of a peak position candidate is present at a position close to the peak position candidate (e.g., within the range of five areas around the peak position candidate), the phase map generation section 114 may pass over the peak position candidate. This makes it possible to prevent a situation in which a plurality of peak positions are situated within a narrow range.

The phase map generation section 114 thus detects the peak position from the principal component score scatter diagram. In the example illustrated in FIG. 17, as a result of performing the process described above and narrowing down a peak position, the phase map generation section 114 has determined the area indicated by both the diagonal lines that extend from upper right to lower left and the diagonal lines that extend from upper left to lower right to be the peak position.

The phase map generation section 114 detects a plurality of peak positions from the principal component score scatter diagram. In the example illustrated in FIG. 15, the phase map generation section 114 detects five peak positions.

The phase map generation section 114 calculates a distance between each point and each peak position on the principal component score scatter diagram, and classifies each point on the principal component score scatter diagram into a plurality of groups based on the calculated distance. For example, the phase map generation section 114 classifies each point on the principal component score scatter diagram so that each point belongs to a group (a cluster) that corresponds to the peak position that is situated at the shortest distance from each point.

Figure 18:
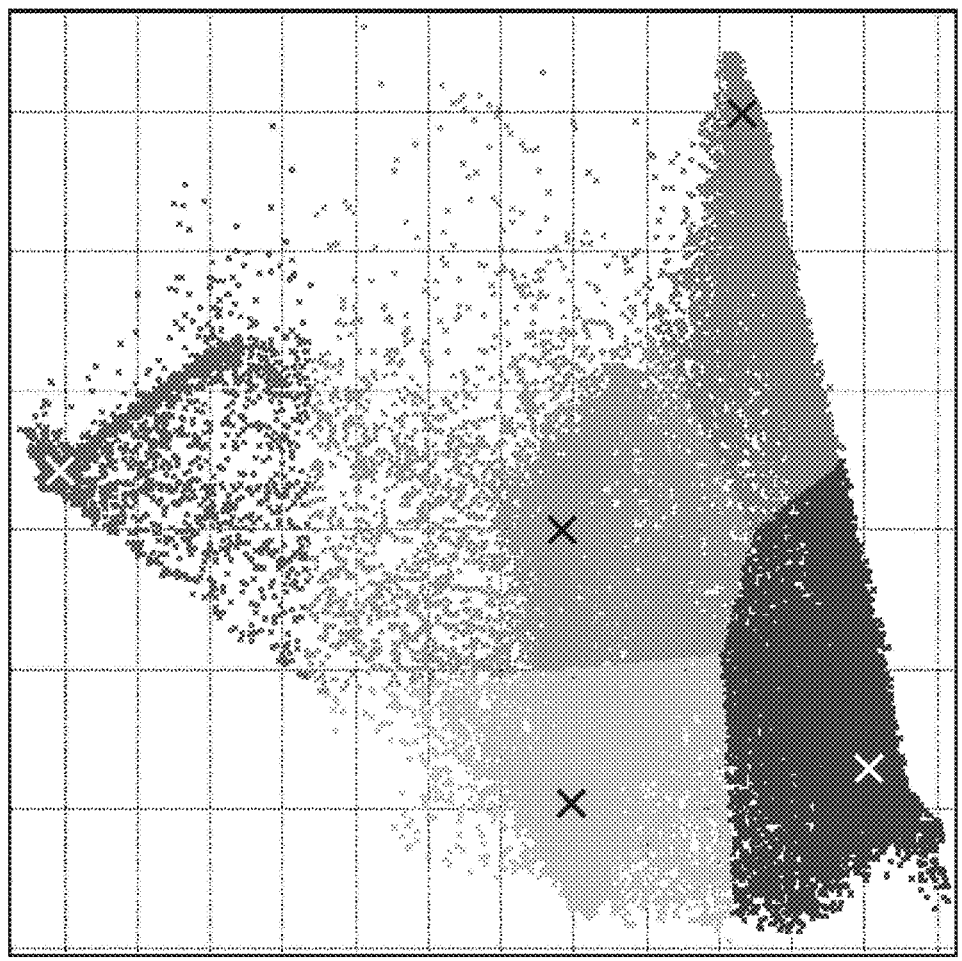
FIG. 18 illustrates a principal component score scatter diagram that is color-coded for each group.

FIG. 18 illustrates the principal component score scatter diagram that is color-coded for each group. In the example illustrated in FIG. 18, each group is indicated by shading. In FIG. 18, each symbol "×" indicates a peak position. The phase map generation section 114 calculates a Euclidean distance between each point and each peak position on the principal component score scatter diagram, and classifies each point on the principal component score scatter diagram so that each point belongs to a group that corresponds to a peak position that is situated at a shortest distance from each point. In the example illustrated in FIG. 18, the phase map generation section 114 classifies each point on the principal component score scatter diagram into five groups since five peak positions have been detected by the phase map generation section 114.

For example, the phase map generation section 114 classifies each point on the principal component score scatter diagram so that each point belongs to any one of the groups. Note that the phase map generation section 114 may not classify, into any group, a point on the principal component score scatter diagram that is situated at a distance longer than a predetermined value with respect to each peak position. For example, the phase map generation section 114 does not classify a point (an outlier point) that is situated at a distance longer than a value obtained by multiplying the sigma value of each peak position by a (where a is an arbitrary number). The phase map generation section 114 may be configured to operate in a mode in which the phase map generation section 114 classifies each point on the scatter diagram to belong to any one of the groups, or a mode in which the phase map generation section 114 does not classify an outlier point into any group. The device (the analyzer) may be configured so that the user can switch the operation mode of the phase map generation section 114 between these modes.

Figure 19:
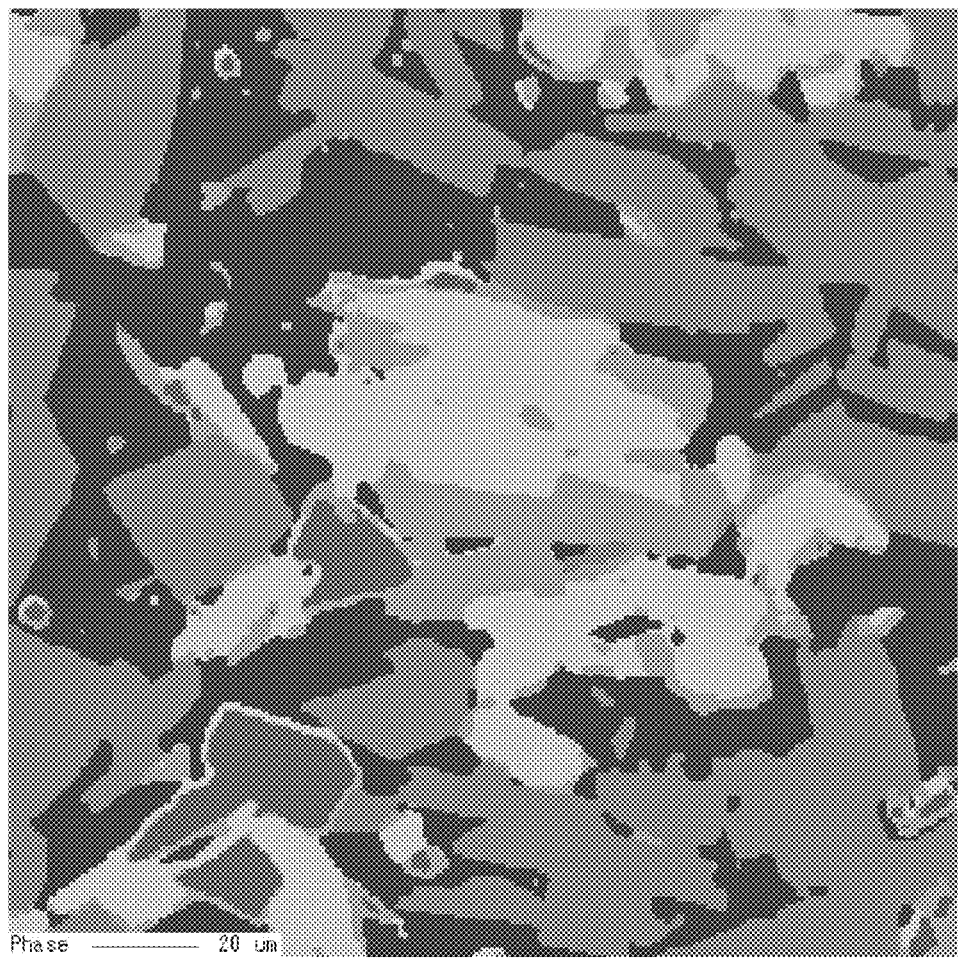
FIG. 19 illustrates an example of a phase map generated by a phase map generation section.

The phase map generation section 114 generates a phase map based on the classification results. The phase map generation section 114 returns each point on the principal component score scatter diagram that is color-coded for each group to the corresponding pixel (unit area) of the elemental map data to generate a phase map in the form of elemental map data. FIG. 19 illustrates an example of a phase map generated by the phase map generation section 114. As illustrated in FIG. 19, the phase map represents the distribution of the groups (clusters).

The phase map generation section 114 thus generates the phase map.

The display control section 116 performs control for causing an image illustrating a result of a phase analysis to be displayed by the display section 122. Specifically, the display control section 116 performs control for causing a phase map generated by the phase map generation section 114 to be displayed by the display section 122. Furthermore, the display control section 116 generates a pie chart representing X-ray intensities of elements as an area on the display section 122 for each phase of a compound included in the generated phase map, and performs control for causing the pie chart to be displayed by the display section 122.

Figure 20:
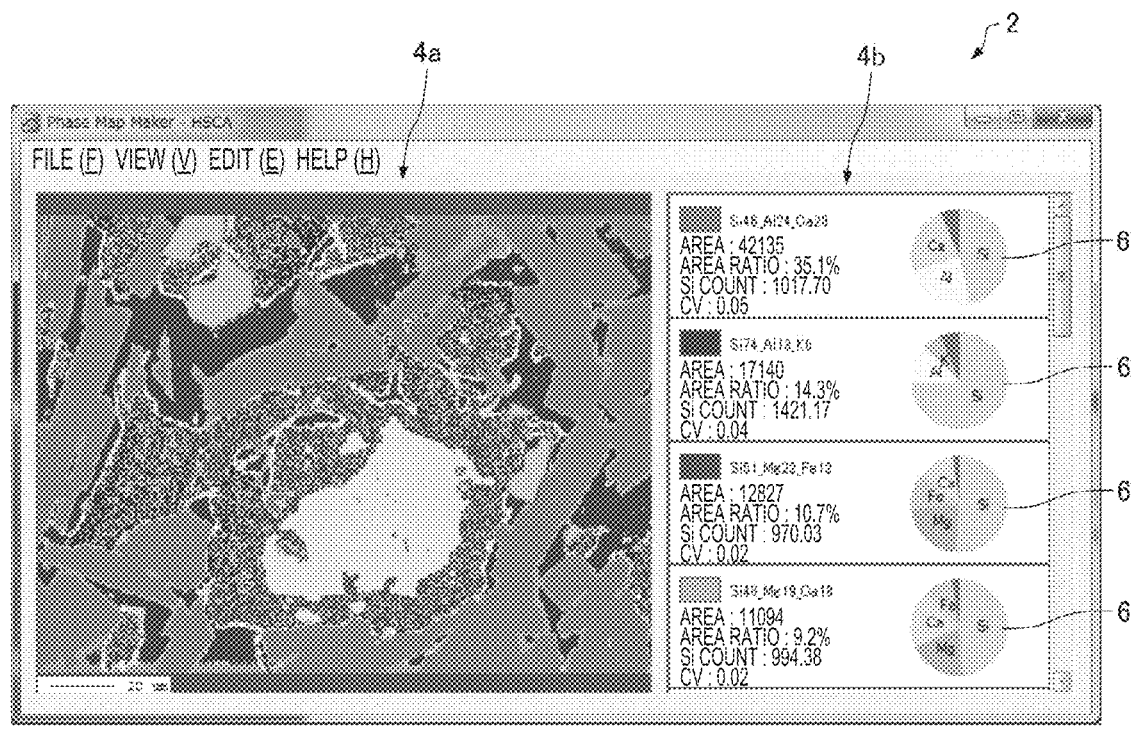
FIG. 20 is an image illustrating results of a phase analysis.

FIG. 20 is an image 2 illustrating results of a phase analysis.

As illustrated in FIG. 20, the image 2 includes a phase map 4a and a parameter area 4b. The phase map 4a and the parameter area 4b (pie charts 6) are displayed in a single window.

In the parameter area 4b, each of the pie charts 6 is displayed together with a name of a phase, an area of the phase, an area ratio of the phase, a name of an element with a highest X-ray intensity in the phase, an average value of an X-ray count (X-ray intensity) of the element with the highest X-ray intensity, a CV (coefficient of variation) value of the element with the highest X-ray intensity, and the like.

In the parameter area 4b, phases are arranged in a descending order of areas occupied by the phases in the phase map. In other words, the pie charts 6 are arranged in a descending order of areas occupied by the phases in the phase map. Note that when a compound included in the phase map has a large number of phases and the parameter areas 4b displaying parameters of the respective phases including the pie chart 6 do not fit into a single window, a display area can be moved using a scroll bar.

Figure 21:
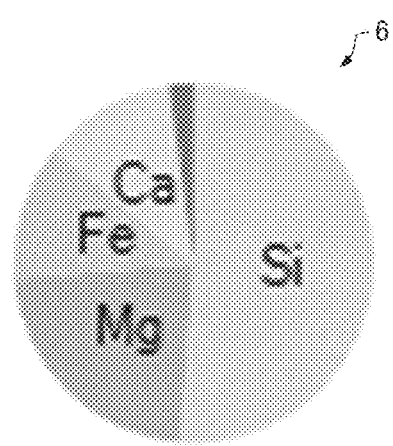
FIG. 21 illustrates an example of a pie chart.

FIG. 21 illustrates an example of the pie chart 6.

The pie chart 6 is a pie chart representing an X-ray intensity of each element in a phase. In the pie chart 6, the higher the X-ray intensity of an element, the greater the area. In the pie chart 6, elements are arranged clockwise in a descending order of X-ray intensities of the elements. Note that, in the pie chart 6, elements with a proportion that is lower than a predetermined proportion are consolidated into one item. In the pie chart 6, a fan-shaped area representing each element is displayed in a different color for each element.

As the name of a phase displayed in the parameter area 4b, three elements with highest X-ray intensities (counts) among the elements included in the phase and proportions of the X-ray intensities of the elements are written in a row. The area of the phase displayed in the parameter area 4b is an area of the phase on the phase map and is expressed in number of pixels. The area ratio of the phase displayed in the parameter area 4b is a proportion of the area of the phase to an entire area (the number of pixels) of the phase map.

2. Operations of Image Processing Apparatus

Figure 22:
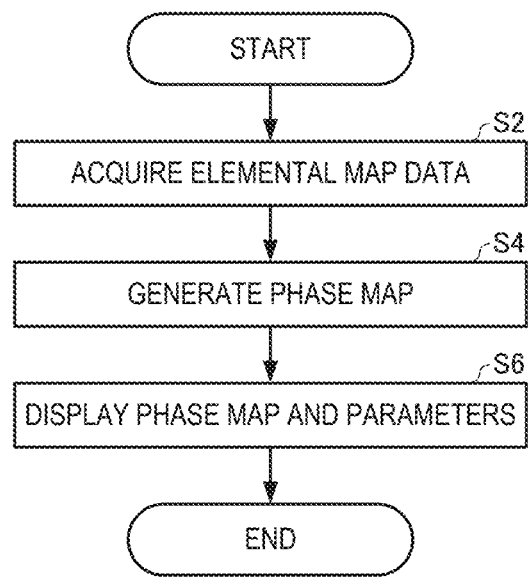
FIG. 22 is a flowchart illustrating an example of a flow of operations of an image processing apparatus according to one embodiment of the invention.

Next, operations of the image processing apparatus 100 according to one embodiment of the invention will be described. FIG. 22 is a flowchart illustrating an example of a flow of operations of the image processing apparatus 100.

First, the elemental map data acquisition section 112 acquires, for each element, elemental map data indicating a distribution of X-ray intensities (S2). The elemental map data is data obtained as a result of performing an area analysis with the surface analyzer main body 10.

Next, the phase map generation section 114 generates a phase map based on the elemental map data acquired by the elemental map data acquisition section 112 (S4).

The display control section 116 then performs control for causing the phase map generated by the phase map generation section 114 to be displayed by the display section 122. In addition, the display control section 116 performs control for causing various parameters (the parameter area 4b) in the phase map to be displayed by the display section 122 (S6). At this point, the display control section 116 performs control for causing the display section 122 to display a pie chart representing X-ray intensities of elements of a phase for each phase of a compound included in the phase map. As a result, the phase map 4a and the parameter area 4b illustrated in FIG. 20 are displayed on the display section 122.

3. Features

The image processing apparatus 100 has the following features, for example.

The image processing apparatus 100 includes: the elemental map data acquisition section 112 that acquires elemental map data representing a distribution of X-ray intensity of each element; the phase map generation section 114 that generates a phase map indicating a distribution of phases of compounds based on the elemental map data; and the display control section 116 that generates a pie chart representing X-ray intensity of each element as an area and performing control so as to cause the display section 122 to display the pie chart for each phase of a compound included in the phase map. Therefore, with the image processing apparatus 100, the X-ray intensity of each element can be displayed as a pie chart on the display section 122. As a result, characteristics of an elemental composition of each phase can be readily comprehended.

In the image processing apparatus 100, the display control section 116 arranges a pie chart generated for each phase of a compound included in a phase map in a descending order of the areas which the phases occupy in the parameter area 4b. Therefore, with the image processing apparatus 100, the pie chart of each phase can be displayed on the display section 122 by being arranged in a descending order of the areas occupied by the phases in the phase map. As a result, a pie chart of an object phase may be readily located.

In the image processing apparatus 100, the display control section 116 consolidates a plurality of elements of which X-ray intensity is lower than a predetermined value into one item of a pie chart. Therefore, in the image processing apparatus 100, a plurality of elements of which X-ray intensity is lower than a predetermined value can be displayed on the display section 122 by being consolidated into one item of a pie chart. As a result, a situation where a large number of items (elements) are displayed on a pie chart and the pie chart becomes messy can be avoided, and elements of interest with high X-ray intensities are made easily viewable on the pie chart.

In the image processing apparatus 100, the display control section 116 performs control for causing a phase map and pie charts to be displayed together on the display section 122. Therefore, with the image processing apparatus 100, a phase map and a pie chart indicating X-ray intensities of elements of each phase can be displayed together on the display section 122. As a result, the X-ray intensities of elements of each phase of the phase map can be readily comprehended.

Since the surface analyzer 1000 includes the image processing apparatus 100, a phase map and characteristics of an elemental composition of each phase can be displayed on the display section 122 in an easily understandable manner.

An image processing method according to one embodiment of the invention includes: acquiring elemental map data representing a distribution of X-ray intensity of each element; generating a phase map indicating a distribution of phases of compounds based on the elemental map data; and generating pie charts representing X-ray intensity of each element as an area for the respective phases of the compounds included in the phase map and causing the display section 122 to display the pie charts. Therefore, with the image processing method according to one embodiment of the invention, the X-ray intensity of each element can be displayed in a pie chart on the display section 122. As a result, characteristics of an elemental composition of each phase can be readily comprehended.

4. Modifications

The invention is not limited to the above embodiments. Various modifications can be made of the above embodiments without departing from the scope of the invention.

For example, in the embodiment described above, while the display control section 116 performs control for causing the X-ray intensity of each element to be displayed as a pie chart on the display section 122, the display control section 116 may perform control for causing a concentration (a composition) of each element instead of the X-ray intensity of each element to be displayed as a pie chart on the display section 122. A concentration of an element can be determined from the X-ray intensity of the element.

Figure 23:
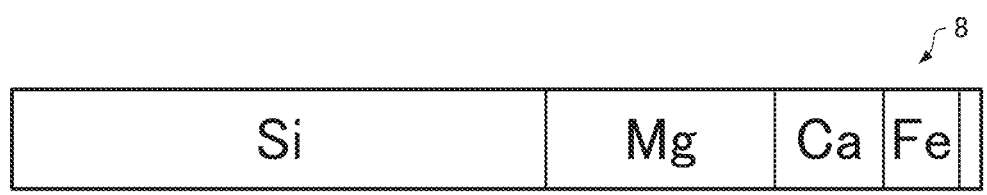
FIG. 23 illustrates an example of a bar chart of X-ray intensity of each element in a phase.
Figures 24, 25:
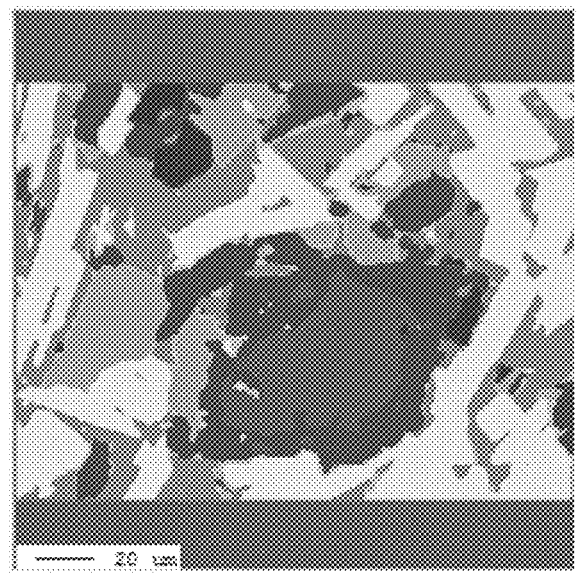
FIG. 24 illustrates an example of a phase map.
FIG. 25 is a list of X-ray intensities of elements of each phase included in a phase map.

In addition, for example, in the embodiment described above, while the display control section 116 performs control for causing the X-ray intensity of each element to be displayed as a pie chart on the display section 122, the display control section 116 may perform control for causing the X-ray intensities of the respective elements of a phase to be displayed as a bar chart 8 on the display section 122 as illustrated in FIG. 23. The bar chart 8 is a graph which represents the X-ray intensity of an element as an area and which represents the X-ray intensity of an element as a rectangle. In the present modification, since the X-ray intensity of each element can be displayed on the display section 122 as the bar chart 8, characteristics of an elemental composition of each phase can be readily comprehended.

Although the above embodiments illustrate an example in which the surface analyzer 1000 is an electron probe microanalyzer (EPMA), the surface analyzer is not limited to an electron probe microanalyzer (EPMA) as long as the surface analyzer is a device that can acquire elemental map data. For example, the surface analyzer may be a scanning electron microscope (SEM) that is provided with an Auger electron spectroscope, an X-ray photoelectron spectroscope (XPS), an energy dispersive X-ray spectrometer (EDS), or the like.

In addition, although the above embodiments illustrate an example in which the image processing apparatus 100 is included in the surface analyzer 1000, the image processing apparatus according to the invention need not necessarily be included in the surface analyzer. For example, the image processing apparatus according to the invention may acquire elemental map data by reading elemental map data stored in an information storage medium.

It should be noted that the embodiments and the modifications described above are merely examples and the invention is not limited thereto. For example, the respective embodiments and the respective modifications may be combined as appropriate.

The invention includes various other configurations which are substantially the same as the configurations described in the embodiments (for example, configurations having the same functions, methods, and results or configurations having the same objectives and effects). In addition, the invention includes various other configurations obtained by replacing nonessential portions of the configurations described in the embodiments. Furthermore, the invention includes various other configurations capable of producing the same effects or configurations capable of achieving the same objectives as the configurations described in the embodiments. Moreover, the invention includes various other configurations obtained by adding known art to the configurations described in the embodiments.

While some embodiments of the invention have been described in detail above, a person skilled in the art will readily appreciate that various modifications can be made without materially departing from the novel teachings and effects of the invention. Accordingly, all such modifications are assumed to be included in the scope of the invention.

What is claimed is:

1. A surface analyzer image processing apparatus, comprising a processor and a memory, the processor configured to execute a program stored in the memory to:
   acquire, from a surface analyzer main body analyzing a surface of a sample, elemental map data representing a distribution of X-ray intensity or a distribution of concentration for each element on the surface of the sample;
   generate a phase map of the surface of the sample indicating a distribution of phases of compounds based on the elemental map data and cause a display section to display the phase map; and
   generate graphs representing X-ray intensity of each element or a concentration of each element as an area for the respective phases of the compounds included in the phase map and cause the display section to display the graphs.

2. The surface analyzer image processing apparatus according to claim 1, wherein, when causing the display section to display the graphs, the graphs are arranged in a descending order of areas occupied by the phases in the phase map.

3. The surface analyzer image processing apparatus according to claim 1, wherein the graphs are pie charts or bar charts.

4. The surface analyzer image processing apparatus according to claim 1, wherein, when causing the display section to display the graphs, a plurality of elements each having a proportion of X-ray intensity or concentration that is lower than a predetermined proportion are consolidated into one item in the respective graphs.

5. The surface analyzer image processing apparatus according to claim 1, wherein, when causing the display section to display the graphs, the display section displays the phase map together with the graphs.

6. A surface analyzer, comprising:
   a surface analyzer main body configured to:
      apply an electron beam to a sample;
      detect characteristic X-rays generated from the sample; and
      analyze a surface of the sample to generate elemental map data representing a distribution of X-ray intensity or a distribution of concentration for each element on the surface of the sample; and
   an image processing apparatus comprising a processor and a memory, the processor configured to execute a program stored in the memory to:
      acquire, from the surface analyzer main body, the elemental map data;
      generate a phase map of the surface of the sample indicating a distribution of phases of compounds based on the elemental map data and cause a display section to display the phase map; and
      generate graphs representing X-ray intensity of each element or a concentration of each element as an area for the respective phases of the compounds included in the phase map and cause the display section to display the graphs.

7. A surface analyzer image processing method, comprising:
- acquiring, with a surface analyzer image processing apparatus and from a surface analyzer main body analyzing a surface of a sample, elemental map data representing a distribution of X-ray intensity or a distribution of concentration for each element on the surface of the sample;
- generating, with the surface analyzer image processing apparatus, a phase map of the surface of the sample indicating a distribution of phases of compounds based on the elemental map data and causing a display section to display the phase map; and
- generating, with the surface analyzer image processing apparatus, graphs representing X-ray intensity of each element or a concentration of each element as an area for the respective phases of the compounds included in the phase map and causing the display section to display the graphs.

* * * * *